United States Patent [19]

Davis

[11] Patent Number: 4,973,760
[45] Date of Patent: Nov. 27, 1990

[54] AROMATIC DIAMINES
[75] Inventor: Robert L. Davis, Baton Rouge, La.
[73] Assignee: Ethyl Corporation, Richmond, Va.
[21] Appl. No.: 254,856
[22] Filed: Oct. 7, 1988
[51] Int. Cl.$^5$ ........................................... C07C 149/42
[52] U.S. Cl. .................................... 564/440; 521/159; 528/64
[58] Field of Search ....................... 564/440; 521/159; 528/64

[56]       References Cited
U.S. PATENT DOCUMENTS

| 4,146,688 | 3/1979 | Schwindt et al. | 521/159 |
| 4,594,453 | 6/1986 | Ranken et al. | 564/440 |
| 4,670,598 | 6/1987 | Davis | 564/440 |
| 4,751,330 | 6/1988 | Davis | 564/440 |

Primary Examiner—Mukund J. Shah
Assistant Examiner—Philip Datlow
Attorney, Agent, or Firm—Patricia J. Hogan; Richard J. Hammond

[57]              ABSTRACT

Novel aromatic diamines which are useful as chain extenders for urethane and urea polymers are compounds corresponding to the formula:

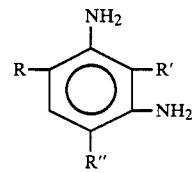

wherein two of the R, R', and R'' substituents are alkyl groups containing 1-6 carbons and the other substituent is a hydrocarbylthio group containing 1-6 carbons.

10 Claims, No Drawings

AROMATIC DIAMINES

FIELD OF INVENTION

This invention relates to aromatic diamines and more particularly to substituted meta-phenylenediamines which can be used as chain extenders for urethane and urea polymers.

BACKGROUND

As disclosed in U.S. Pat. No. 4,146,688 (Schwindt et al.), it is known that phenylenediamines which bear a single ar-hydrocarbylthio substituent and optionally also a single ar-alkyl substituent can be used as chain extenders for polyurethane resins. However, the use of these known chain extenders can create toxicity and/or discoloration problems.

U.S. Pat. No. 4,595,742 (Nalepa et al.) discloses phenylenediamine chain extenders which bear at least two ar-alkylthio substituents and preferably also an ar-alkyl substituent. These chain extenders lack the disadvantages of the chain extenders of Schwindt et al. and are ordinarily quite suitable for the preparation of urethane and urea polymers having desirable properties. However, in some applications, e.g., in the preparation of room temperature coatings and in the preparation of polymers by RIM processes, the gel times provided by the chain extenders are sometimes slower than is desired.

U.S. Pats. No. 4 594,453 et al.), 4,670,598 (Davis-I), and 4,751,330 (Davis-II) teach that phenylenediamines bearing at least one ar-hydrocarbylthio substituent can be prepared by reacting a phenylenediamine, optionally bearing an ar-alkyl substituent, with a hydrocarbyldisulfide in the presence of a Lewis acid catalyst.

SUMMARY OF INVENTION

An object of this invention is to provide novel meta-phenylenediamines.

Another object is to provide such diamines which are useful as chain extenders for urethane and urea polymers.

A further object is to provide such chain extenders which can be used in RIM processes and in the preparation of room temperature coatings.

These and other objects are attained by the provision of meta-phenylenediamines corresponding to the formula:

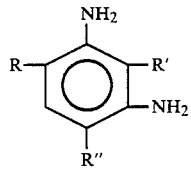

wherein two of the R, R', and R" substituents are alkyl groups containing 1-6 carbons and the other substituent is a hydrocarbylthio group containing 1-6 carbons.

DETAILED DESCRIPTION

The meta-phenylenediamines of the invention may be any compounds corresponding to the above formula, i.e., compounds wherein each of the alkyl groups may be any alkyl group containing 1-6 carbons, such as a methyl, ethyl, propyl, n-butyl, secbutyl, t-butyl, pentyl, or hexyl group, and the hydrocarbylthio group is one in which the hydrocarbyl moiety may be any saturated or unsaturated aliphatic, alicyclic, or aromatic hydrocarbyl moiety containing 1-6 carbons, such as a methyl, ethyl, propyl, n-butyl, sec-butyl, t-butyl, pentyl, hexyl, allyl, methallyl, cyclopentyl, cyclohexyl, or phenyl group. However, the preferred meta-phenylenediamines are those wherein two of the R, R', and R" substituents are alkyl groups containing 1-3 carbons and the other substituent is an alkylthio group containing 1-3 carbons.

Exemplary of the preferred meta-phenylenediamines are the 2-alkylthio-4,6-dialkyl-1,3-diaminobenzenes such as 2-methylthio-4,6-dimethyl-1,3-diaminobenzene, 2-ethylthio-4,6-diisopropyl-1,3-dimethyl-1,3-diaminobenzene, and 2-methylthio-4,6-diisopropyl-1,3-diaminobenzene; the 4-alkylthio-2,6-dialkyl-1,3-diaminobenzenes such as 4-methylthio-2,6-dimethyl-1,3-diaminobenzene, 4-ethylthio-2,6-dimethyl-1,3-diaminobenzene, and 4-methylthio-2,6-diisopropyl-1,3-diaminobenzene; and mixtures thereof.

The compounds of the invention may be prepared by known techniques, such as by using the processes of Ranken et al., Davis-I, or Davis-II (the teachings of all of which are incorporated herein in toto by reference) to substitute a hydrocarbylthio group onto the ring of a 2,6- or 4,6-dialkyl-1,3-diaminobenzene which, when not commercially available, may be prepared by the alkylation of meta-phenylenediamine or by the nitration and reduction of the appropriate dialkylbenzene, as in U.S. Pat. No. 4,526,905 (Lucast et al.), the teachings of which are also incorporated herein in toto by reference. However, they may also be prepared by a modification of the Ranken et al./Davis-I/-Davis-II hydrocarbylthiation processes utilizing an iodine catalyst or a nitrogen sparge, as taught in copending applications Ser. No. 254,857 (Knapp), filed Oct. 7, 1988, and Ser. No. 254,858 (Simon et al.), filed Oct. 7, 1988, both now abandoned, respectively. Use of the nitrogen sparge technique is apt to be preferred when a hydrocarbyldisulfide having more than one carbon in the hydrocarbyl moiety is used to substitute a hydrocarbylthio group onto the ring of the dialkyl-1,3-diaminobenzene.

The meta-phenylenediamines of the invention are particularly useful as chain extenders for urethane, urea, and urethaneurea polymers which, like those of the prior art, are prepared by reacting the chain extender with (1) an organic polyisocyanate and an active hydrogen-containing organic compound or (2) a prepolymer thereof having a free -NCO content of at least 0.1% by weight. The organic polyisocyanates and active hydrogen-containing organic compounds, or prepolymers thereof, which are reacted with the chain extenders may be any such materials which are conventionally employed in the preparation of urethane, urea, and urethane-urea polymers, such as those taught in Nalepa et al., the teachings of which are incorporated herein in toto by reference. However, since a particular advantage of the novel chain extenders is their providing gel times which are slower than those obtained with very reactive chain extenders, such as dialkyltoluenediamines, and faster than those obtained with relatively slow chain extenders, such as di(alkylthio)toluenediamines, they are especially of interest for use in the preparation of room temperature coatings and in the preparation of polymers by RIM processes -- applications in which the materials reacted with chain extenders are generally diphenylmethanediisocyanate (MDI) or toluenediisocyanate (TDI) prepolymers.

The following examples are given to illustrate the invention and are not intended as a limitation thereof.

EXAMPLE I

Part A

A suitable reaction vessel was charged with 7.9 L of a 5.5/1 by volume mixture of concentrated sulfuric acid and 90% nitric acid. After the acid mixture had been cooled to −10° C., 1970 g of 1,3-diisopropylbenzene was added with stirring at a rate such as to maintain a reaction temperature between −10° C. and 0° C., stirring was continued for an additional two hours, and the reaction mixture was then allowed to warm to ambient temperature. The excess acid was then diluted to about 25–30% by the addition of ice, after which the solid product was filtered by suction and washed once with water, once with 5% aqueous sodium carbonate, and once again with water.

Part B

The moist solid product of Part A was charged to a suitable reaction vessel, followed by 17 L of toluene and 40 g of 5% Pd/C catalyst. The solid was then hydrogenated at 95° C. and 5.2 MPa of hydrogen to convert the nitro groups in the starting material to amino groups. After hydrogenation was complete, the catalyst was removed by filtration and the toluene stripped in a rotary evaporator. The residue was vacuum-distilled from 1% solid NaOH. The reaction resulted in the formation of 1436 g (61.5% yield) of a mixture of 4,6- and 2,6-diisopropyl-1,3-diaminobenzenes having a melting point of 53°–56° C.

Part C

A suitable reaction vessel was charged with a mixture of 630 g of the product of Part B and 31.2 g of anhydrous cuprous iodide, which was then heated to 145° C. Dimethyldisulfide was added dropwise to maintain a reflux temperature of 145° C., and progress of the reaction was followed by periodically taking aliquots of the reaction mixture and analyzing them by gas chromatography. After 3.5 hours, 620 mL of dimethyldisulfide had been added and no further reaction was apparent.

The mixture was then cooled to 110° C., 33 g of solid NaOH was added, and stirring and heating were continued for one hour, after which the mixture was filtered. The filtrate was stripped of excess dimethyldisulfide on a rotary evaporator and the residue flashed in vacuum from 1% solid NaOH. The reaction resulted in a 95.8% yield of a red-colored liquid which GC and GC/MS analyses showed to contain 99.6% of a 5.5/1 mixture of 2-methylthio-4,6-diisopropyl-1,3-diaminobenzene and 4-methylthio-2,6diisopropyl-1,3-diaminobenzene.

EXAMPLE II

Part A

Parts A and B of Example I were essentially repeated except that the starting reaction mixture was obtained by adding a mixture of 1720 g of 70% nitric acid and 12,285 g of concentrated sulfuric acid to 1379 g of m-xylene, and the temperature maintained for the nitration reaction was 10° C. The nitration and hydrogenation resulted in the formation of 1275 g (72.1% yield) of a mixture of 4,6- and 2,6-dimethyl-1,3-diaminobenzenes.

Part B

The procedures of Example I, Part C, were used to prepare and recover a product from the reaction of 400 mL of dimethyldisulfide with 330 g of the product of Part A in the presence of 17.3 g of cuprous iodide. The reaction resulted in a 91.6% yield of a waxy, yellow solid which melted at 73°–77° C. and contained 97.1% of a 1.4/1 mixture of 2-methylthio-4,6-dimethyl-1,3-diaminobenzene and 4-methylthio-2,6-dimethyl-1,3-diaminobenzene.

It is obvious that many variation may be made in the products and processes set forth above without departing from the spirit and scope of this invention.

What is claimed is:

1. A meta-phenylenediamine corresponding to the formula:

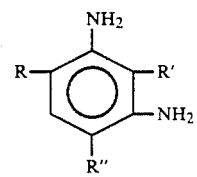

wherein two of the R, R', and R" substituents are alkyl groups containing 1–6 carbons and the other substituent is a hydrocarbylthio group containing 1–6 carbons.

2. The meta-phenylenediamine of claim 1 wherein two of the R, R', and R' substituents are alkyl groups containing 1–3 carbons and the other substituent is an alkylthio group containing 1–3 carbons.

3. The meta-phenylenediamine of claim 2 which is a 2-alkylthio-4,6-dialkyl-1,3-diaminobenzene.

4. The meta-phenylenediamine of claim 3 which is 2-methylthio-4,6-dimethyl-1,3-diaminobenzene.

5. The meta-phenylenediamine of claim 3 which is 2-ethylthio-4,6-dimethyl-1,3-diaminobenzene.

6. The meta-phenylenediamine of claim 3 which is 2-methylthio-4,6-diisopropyl-1,3-diaminobenzene.

7. The meta-phenylenediamine of claim 2 which is a 4-alkylthio-2,6-dialkyl-1,3-diaminobenzene.

8. The meta-phenylenediamine of claim 7 which is 4-methylthio-2,6-dimethyl-1,3-diaminobenzene.

9. The meta-phenylenediamine of claim 7 which is 4-ethylthio-2,6-dimethyl-1,3-diaminobenzene.

10. The meta-phenylenediamine of claim 7 which is 4-methylthio-2,6-diisopropyl-1,3-diaminobenzene.

* * * * *

UNITED STATES PATENT AND TRADEMARK OFFICE
CERTIFICATE OF CORRECTION

PATENT NO. : 4,973,760

DATED : November 27, 1990

INVENTOR(S) : Robert L. Davis

It is certified that error appears in the above-identified patent and that said Letters Patent is hereby corrected as shown below:

Column 4, line 42, reads "R, R', and R' " and should read --R, R', and R"--

Signed and Sealed this

Twenty-eighth Day of April, 1992

Attest:

HARRY F. MANBECK, JR.

*Attesting Officer*   *Commissioner of Patents and Trademarks*